United States Patent [19]

Khoobiar

[11] 4,240,930

[45] Dec. 23, 1980

[54] CATALYST AND PROCESS FOR PRODUCING METHACRYLIC ACID

[75] Inventor: Sargis Khoobiar, Kinnelon, N.J.

[73] Assignee: Halcon Research and Development Corp., New York, N.Y.

[21] Appl. No.: 27,632

[22] Filed: Apr. 6, 1979

Related U.S. Application Data

[63] Continuation-in-part of Ser. No. 973,354, Dec. 26, 1978.

[51] Int. Cl.$^3$ ............................................. B01J 27/14
[52] U.S. Cl. ..................................... 252/435; 252/437
[58] Field of Search ................................. 252/435, 437

[56] References Cited

U.S. PATENT DOCUMENTS

| | | | |
|---|---|---|---|
| 3,976,688 | 8/1976 | Akiyama et al. | 252/435 X |
| 4,000,088 | 12/1976 | Shimizu et al. | 252/435 X |
| 4,001,316 | 1/1977 | Ishimi | 252/435 X |
| 4,042,533 | 8/1977 | Shaw et al. | 252/435 X |
| 4,051,179 | 9/1977 | Sorobe et al. | 252/435 X |

FOREIGN PATENT DOCUMENTS 1430337  3/1976  United Kingdom ..................... 252/435

*Primary Examiner*—Delbert E. Gantz
*Assistant Examiner*—William G. Wright
*Attorney, Agent, or Firm*—William C. Long; David Dick; Harold N. Wells

[57] ABSTRACT

A catalyst composition useful for the oxidation of unsaturated aldehydes, particularly the oxidation of methacrolein to produce methacrylic acid, comprises the combination of oxides of molybdenum, copper, phosphorus, antimony, and cesium in predetermined relative atomic ratios.

1 Claim, 2 Drawing Figures

CATALYST AND PROCESS FOR PRODUCING METHACRYLIC ACID

CROSS-REFERENCE TO OTHER APPLICATIONS

This is a continuation-in-part of U.S. Ser. No. 973,354 filed Dec. 26, 1978.

PRIOR ART

This invention relates to a process and catalyst for the vapor-phase oxidation with molecular oxygen of methacrolein to methacrylic acid.

It is well known that unsaturated acids, such as acrylic acid and methacrylic acid, can be produced by the vapor-phase oxidation of the corresponding unsaturated aldehydes by means of molecular oxygen in the presence of a suitable oxidation catalyst. A variety of catalyst compositions have been proposed for this purpose. Many such compositions comprise the oxides of molybdenum and phosphorus in association with the oxides of various other elements, both metallic and non-metallic.

For example, and with respect to the catalyst to be discussed hereafter, British Pat. No. 1,430,337 and U.S. Pat. No. 4,000,088 propose the use of catalyst composition in which the oxides of molybdenum and phosphorus are combined with the oxides of antimony, copper and optionally, chromium. The catalyst does not contain cesium.

U.S. patents in which cesium may be present in similar catalysts include U.S. Pat. Nos. 4,051,179 and 4,042,533. In '179 copper and vanadium are treated as alternatives, while an alkali metal must be included, but antimony is considered optional. In '533 tungsten is required, while copper and phosphorus are optional and antimony is lacking.

Despite the disclosures of the prior art, a catalyst of this type is not formulated merely by combining the many elements which have been disclosed in the prior art. Instead the catalyst performance must be determined experimentally at the expected operating conditions. Small changes in composition may be very important in achieving improved catalyst performance and particularly in optimizing the catalyst composition to suit a specific reaction and set of operating conditions. The point is well illustrated by the improvements in catalyst formulation to be described hereinafter.

It has been found that catalysts for oxidation of methacrolein to methacrylic acid have the characteristic property of remaining stable for a long period of time and then, without warning, of beginning a rapid decline in activity. Consequently, an increase in the useful life of such catalysts has been sought, which has been achieved in the present invention by the addition of a stabilizing ingredient.

SUMMARY OF THE INVENTION

It has been discovered that when using the catalysts to be described to produce methacrylic acid by vapor phase oxidation of methacrolein, it is possible to achieve both high activity and high selectivity for a significantly improved useful life compared to catalysts which lack the stabilizing element of the invention. The catalyst composition comprises oxides of molybdenum, copper, phosphorus, antimony, and cesium in predetermined relative atomic ratios. More specifically, the catalyst composition of the invention comprises the oxides of the above specified elements in the following atomic ratios: Mo=12, Cu=0.05-3, P=0.1-5, Sb=0.1-0.5, and Cs=0.1-3. The catalyst composition may be regarded either as a mixture of oxides of the named elements or as oxygen-containing compounds of the elements or both.

The catalyst composition used in the process of the invention also may be expressed by the following general formula:

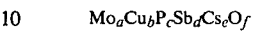

$$Mo_aCu_bP_cSb_dCs_eO_f$$

wherein a to f indicate the atomic ratio of each component and, when a is 12, b is 0.05-3, c is 0.1-5, d is 0.1-0.5, e is 0.1-3, and f has a value which is determined by the valence and proportions of the other elements in the catalyst.

When such a catalyst as has been described is in contact with a vapor-phase mixture of methacrolein, molecular oxygen, steam, and nitrogen at temperatures in the range of 250°–400° C. and pressures in the range of 0–5 atmospheres, excellent activity and selectivity to the production of methacrylic acid is obtained for a longer period of time than for a catalyst lacking cesium.

DESCRIPTION OF THE PREFERRED EMBODIMENTS

Catalyst Composition and Preparation

Figure 1:
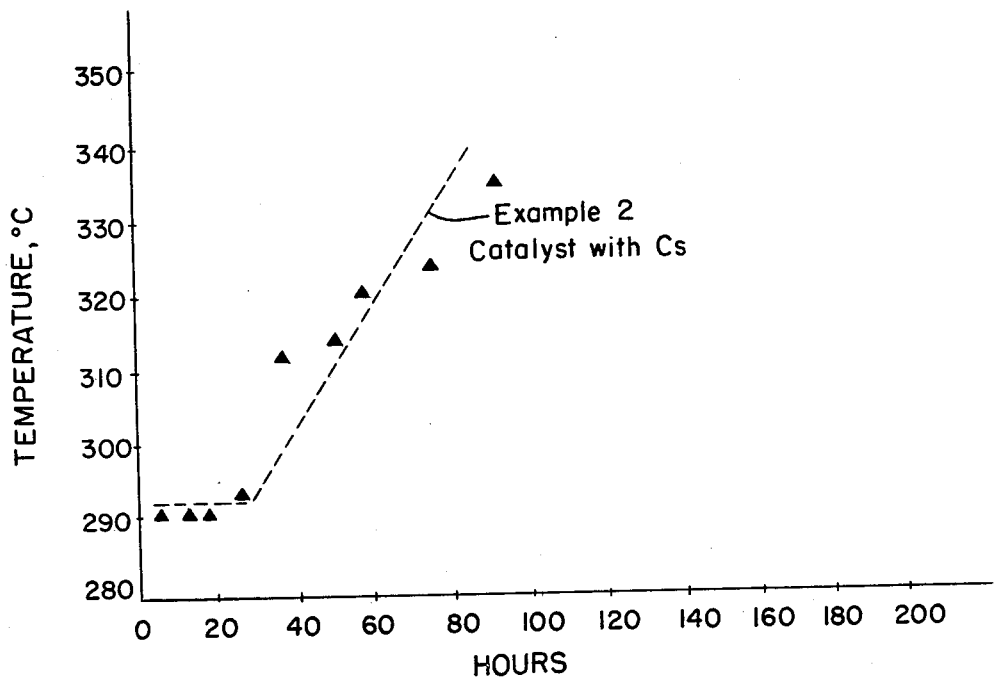
FIG. 1 graphically displays the change of reaction temperature over a period of operation as a comparison of the useful life of oxidation catalysts.

The catalyst of the invention comprises oxides or oxygen-containing compounds of molybdenum, copper, phosphorus, antimony and cesium in predetermined atomic ratios, as expressed in the following general formula: $Mo_aCu_bP_cSb_dCs_eO_f$ wherein a to f indicate the atomic ratio of each component and, when a is 12, b is 0.05-3, c is 0.1-5, d is 0.1-0.5, e is 0.1-6, and f is a value determined by the valence and proportions of the other elements in the catalyst. It has been found that the amount of antimony employed in the catalyst is particularly important. As will be seen later, the addition of antimony in small amounts provides significantly improved conversion of methacrolein and with higher selectivity to methacrylic acid than when no antimony is used. However, further increase of antimony content causes a loss of both conversion and selectivity so that the amount of antimony should be limited to a value of about 0.5. The preferred value is about 0.3. Other elements, which may be included in minor amounts in the catalyst formulation in order to promote catalyst activity or selectivity and without losing the advantages to be shown for the principal formula, are considered to be within the scope of the invention. The catalyst composition may be regarded either as a mixture of oxides of the named elements or as oxygen-containing compounds of the elements or both. As prepared and/or under reaction conditions, the catalyst may contain either or both forms and both are intended to be included within the phrase "mixtures of oxides."

The catalyst composition is preferably used in unsupported form, e.g. in the form of pellets or other like compressed shapes of various sizes although conventional supports could be employed instead. The composition may be formed in conventional manner using techniques well known to persons skilled in the art. For example, compounds of molybdenum, copper, phosphorus, antimony and cesium are dissolved in a small amount of water or other solvent, and the solutions are then combined and evaporated to dryness, e.g. in a rotary dryer. The several components can be introduced into solution in the form of various salts or other compounds of convenient types and no specific form for the catalyst precursors is necessary. The use of ammonium salts, halides e.g. chlorides, nitrates or acid forms of the elements, e.g. phosphoric acid, are, however, particularly suitable. Preferably, however, aqueous solutions are employed and water-soluble forms of the elements are used. In some cases the solutions may have acids and/or bases added to them to facilitate dissolution of the catalyst precursors. For example, acids such as hydrochloric or nitric acid, or bases such as ammonium hydroxide, can be used as desired. The resulting powder from the evaporation is then thoroughly dried and preferably screened to eliminate large particles which make it difficult to produce uniform compressed shapes, such as pellets. Typically, the powder is passed through a 20-mesh screen. The powder is then mixed with an organic binder which can be of any conventional type, such as polyvinyl alcohol, and the mixture is thoroughly dried and again screened, typically to provide a 20–80 mesh size. The dried mixture is then preferably combined with a lubricant, again of any conventional type, such as stearic acid or graphite, and compressed into the desired shape, e.g. pelletized, the compressed shapes typically having heights and diameters of 1/16 inch to ⅜ inch. Finally, the thus produced catalyst composition is activated at high temperature for a prolonged period in accordance with conventional practice in this art. For example, the pellets are placed in an oven or kiln, or in a tube through which air is passed, at an elevated temperature (e.g. 300°–500° C., preferably 325°–450° C.) for at least ten hours. In a particularly preferred activation step, the temperature is raised at the rate of 20° C. per hour to a maximum of 420° C., preferably 320°–400° C., and this temperature is maintained for 16 hours.

It will be understood that the foregoing description regarding preparation of the catalyst in a form suitable for use in a vapor-phase oxidation reaction is merely illustrative of many possible preparative methods, although it is a particularly suitable method and is preferred.

Methods of Operation

The catalysts described are generally useful for the production of unsaturated acids by oxidation with molecular oxygen of unsaturated aldehydes, although the reaction of methacrolein to form methacrylic acid is of particular interest. Other possible starting materials are the monoethylenically unsaturated aliphatic monoaldehydes of from 3 to 6 carbon atoms, such as acrolein, crotonaldehyde, 2-methyl-2-butenal, and the like, or mixtures thereof.

The reaction in which the catalyst compositions of this invention are of particular utility and in which they provide high conversions and selectivities involves contacting the catalyst with methacrolein and oxygen in the vapor phase, preferably also in the presence of steam and diluents. When the catalyst of this invention is used in the vapor-phase oxidation of methacrolein to form methacrylic acid, the oxidation conditions employed are those generally associated with this reaction, although the molar ratio of oxygen to methacrolein should be kept at a high value near the flammable range in order to obtain the longest useful catalyst life. Once reaction is begun, it is self-sustaining because of its exothermic nature. A variety of reactor types may be employed, such as fluid or fixed bed types, but reactors having the catalyst disposed inside a multiplicity of heat exchanger tubes are particularly useful and convenient.

The gaseous feed to the reactor contains appropriate concentrations of methacrolein, oxygen and steam and usually an inert gas, such as nitrogen, is also present. The oxygen is usually added as such or as air, which may be enriched with oxygen. As mentioned, conventional oxidation conditions can be employed but it is a feature of the catalyst of this invention that the methacrolein can be present in concentrations of more than 5 up to about 20 volume percent of the total feed with a preferred range of more than 5 up to about 15 volume percent. In general at least 6 volume percent of the aldehyde is used in the feed. The corresponding ranges for oxygen are 3 to 15 volume percent, preferably 5 to 12 volume percent and for steam up to 50 volume percent, preferably 5 to 35 volume percent, the balance being the inert gas or gases.

The temperature of the reaction should, for best results, be within the range of from about 270° to 450° C., preferably 280°–400° C., and the optimum temperature range is 290° to 325° C. Because the reaction is exothermic, means for conducting the heat away from the reactor are normally employed to avoid a temperature increase which favors the destruction of methacrolein by complete oxidation to carbon dioxide and water. The reactor temperature may be controlled by conventional methods such as by surrounding the catalyst-containing tubes with a molten salt bath.

The reaction may be conducted at atmospheric, superatmospheric or subatmospheric pressure. Preferably, however, pressures ranging from atmospheric up to about 8 kg/cm² absolute, preferably up to about 6.3 kg/cm² absolute, and most preferably up to about 4.5 kg/cm² absolute are employed.

The unsaturated acid product may be recovered by a number of methods well known to those skilled in the art. For example, the acid may be condensed, or scrubbed with water or other suitable solvents, followed by separation of the unsaturated acid product from the scrubbing liquid. The gases remaining after the acid-removal step are suitably recycled to the reaction, if desired, preferably after removal of $CO_2$ by conventional means, e.g., absorption in aqueous carbonate solution.

The features of the invention will be more readily apparent from the following specific examples of typical catalyst preparation and its use in the oxidation of methacrolein. It will be understood, however, that these examples are for the purpose of illustration only and are not to be interpreted as limiting the invention.

EXAMPLE 1

In 750 cc of water are dissolved 636 grams of $(NH_4)_6Mo_7O_{24}.4H_2O$. Then 21.7 grams of $Cu(NO_3)_2.3H_2O$ are dissolved in 100 cc of water, 58.4 grams of $CsNo_3$ are dissolved in 300 cc of water, 20.5 grams of $SbCl_3$ are dissolved in a mixture of 30 cc of water, and 10 cc of concentrated HCl and 34.5 grams of $H_3PO_4$ are dissolved in a mixture of 100 cc of water. These solutions are fed to a rotary dryer of 4000 cc capacity and the mixture is evaporated to dryness at a temperature of 140° C. The resulting powder is removed from the dryer and dried in an oven at 200° C. for 12 hours. The dried powder is screened through a 20-mesh screen, a 4% aqueous solution of polyvinyl alcohol is added in sufficient quantity to make a damp mixture and this mixture is dried at 75°–80° C. until the moisture content falls to 2–4 wt. %. The dried mixture is then screened to 20–80 mesh size particles, and about 2–6% of stearic acid powder is thoroughly mixed with it. The resulting mixture is then pelletized to form pellets of 3/16 inch height and diameter in which the catalyst components molybdenum, copper, phosphorus, antimony, and cesium are present in the atomic ratios of 12, 0.3, 1, 0.3 and 1, respectively. The pellets are then activated in an oven by heating them gradually at a rate of 20° C. per hour to 380° C. and maintaining them at this temperature for 16 hours. The activated pellets have a density of 0.97 gm/cc.

EXAMPLE 2

A 150 cc quantity of the catalyst composition is placed in a reactor defined by a $\frac{1}{2}'' \times 90'$ stainless steel pipe, the reactor pipe being filled with 50 cc of inert filler (silicon carbide) below the catalyst bed and 100 cc of the inert filled above the catalyst bed in conventional manner to insure uniform temperature contact with the catalyst. Nitrogen-diluted mixtures containing methacrolein, oxygen and steam are fed to the reactor at a pressure of 1.74 kg/cm$^2$ (absolute) and at a space velocity of about 1200 hr$^{-1}$. The term "space velocity" is used in its conventional sense to mean liters of gas (at standard temperature and pressure) per liter of catalyst per hour. The feed composition is approximately, by volume, 6–7% methacrolein, 11–12% oxygen and 20% steam, the balance being nitrogen, determination being made on a wet basis. The reaction is run continuously and the exit gas is analyzed at intervals of several hours to give the overall effect of a series of different runs. Analyses are carried out by means of gas chromatography and by infrared spectrography using conventional techniques.

For comparison of many catalysts, all of which are capable of providing a satisfactory yield of methacrylic acid, but which differ in their useful life, an accelerated aging test is carried out on the catalyst of Example 1 and reported in the sole figure. The catalyst is tested under severe conditions in order to obtain relatively quick determination of the catalyst performance by raising the operating temperature to the level needed to achieve at least about 80% conversion of methacrolein to methacrylic acid. For commercial operation, the temperature most suitable for obtaining the best yield of methacrylic acid for a long period of useful catalyst life would be selected. As the catalyst deactivates, it is necessary to raise the operating temperature to maintain a constant degree of methacrolein conversion. The upper limit of catalyst temperature is reached when the target of 80% conversion can no longer be obtained. This is generally found to be at about 325°–330° C. At that point, the catalyst is no longer useful. While for commercial operation a useful life of at least 2–3000 hours is desired, by means of the accelerated aging test, even durable catalysts can be fully deactivated within about 100 hours, thus providing catalyst life information which might be obtained only after thousands of hours under more conventional conditions.

The performance of a catalyst containing cesium is shown in the figure. The useful life in the accelerated test of a catalyst containing cesium (Example 3) is about 70 hours and it begins to lose activity after an induction period of about 30 hours. The performance of a catalyst containing no cesium is markedly inferior as will be seen in the following comparative example.

COMPARATIVE EXAMPLE

EXAMPLE 3

A catalyst corresponding to that of Example 1 is prepared by the same technique except no cesium nitrate is included in the initial solution to provide a catalyst similar to that of U.S. Pat. No. 4,000,088 and having the following nominal composition:

$Mo_{12}Cu_{0.3}P_1Sb_{0.3}O_i$

When the catalyst is tested under the conditions of Example 2 it is found that the results cannot be plotted in the figure for comparison with Example 2. Even at 370° C., only 50% conversion of methacrolein was obtained, with 70% selectivity to methacrylic acid. Since the figure shows the temperature required to obtain 80% conversion, it is not possible to plot the results.

The advantage of adding cesium is apparent when comparing the results of Examples 2 and 3. With no cesium present, the catalyst is not capable of reaching a high conversion level, which is important for commercial application. Example 3 indicates that addition of the alkali metal cesium improves the catalyst of Example 1.

EXAMPLE 4

In order to demonstrate the importance of antimony in the catalyst of the invention, several catalysts were prepared according to Example 1, but the antimony content was varied. The catalysts were tested under the conditions of Example 2 except that no attempt was made to reach 80% conversion of methacrolein, but instead a determination was made to the lowest temperature at which a satisfactory conversion and selectivity could be obtained. The results are shown in the following table.

| Sb Content | Reactor Temp. °C. | Methacrolein Conversion, % | Selectivity % to Methacrylic Acid |
|---|---|---|---|
| 0 | 288 | 49 | 61 |
| 0.3 | 296 | 70 | 78 |
| 0.5 | 294 | 55 | 75 |

Figure 2:
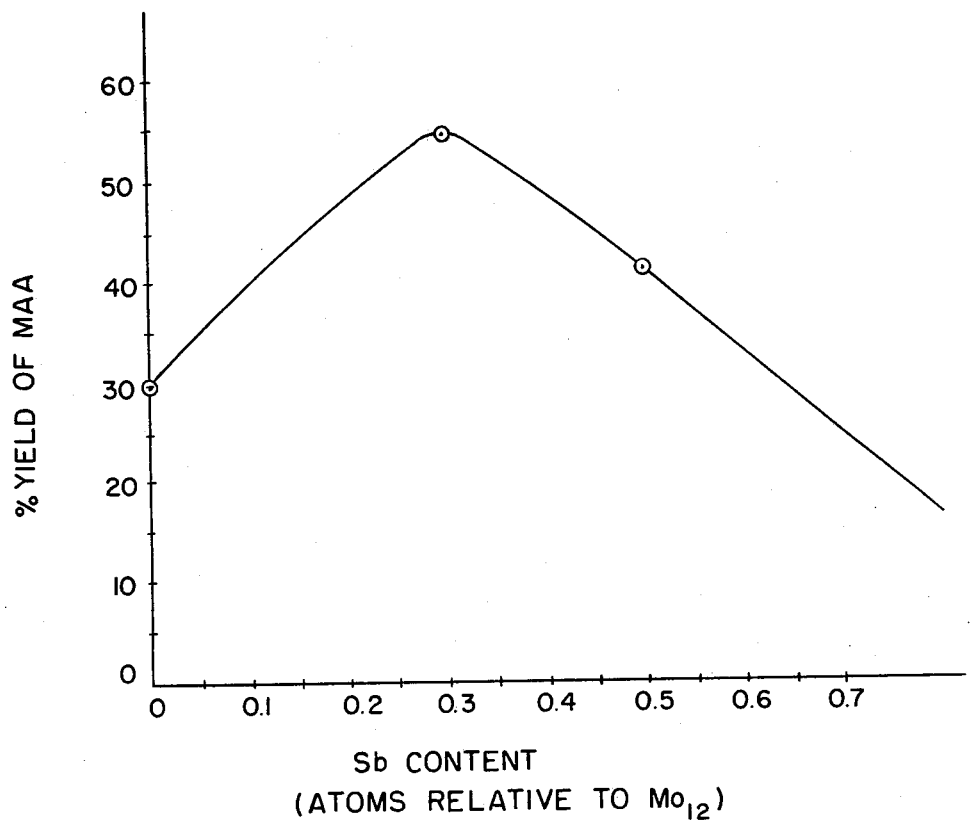
FIG. 2 shows the effect of varying the antimony content of catalysts according to the invention.

The data from the table are plotted in FIG. 2 which makes clear the critical importance of the antimony content in catalysts of this formulation. For purposes of the figure, the conversion and selectivity figures are multiplied to provide a percentage yield of methacrylic acid (MAA) from the methacrolein fed. The yield of methacrylic acid is of particular importance with regard to commercial use of such catalysts, since the by-products are of lesser value. The figure clearly indicates that addition of antimony raises the yield of methacrylic acid remarkably, but that the yield appears to be maximized between say 0.1 and 0.5 and that about 0.3 is a preferred value. Further, by extrapolation, it appears likely that beyond about 0.6, addition of antimony gives a yield worse than that obtained with no antimony at all.

What is claimed is:

1. A catalyst composition suitable for the vapor-phase oxidation of methacrolein to produce methacrylic acid consisting essentially of the oxides of molybdenum, copper, phosphorus, antimony and cesium and having the formula $Mo_aCu_bP_cSb_dCs_eO_f$, where: $a=12$; $b=0.05-3$; $c=0.1-5$; $d=0.1-0.5$; $e=0.1-3$; and $f=$ value determined by the valence and proportions of the other elements of the formula.

* * * * *

UNITED STATES PATENT AND TRADEMARK OFFICE
CERTIFICATE OF CORRECTION

PATENT NO. : 4,240,930
DATED : December 23, 1980
INVENTOR(S) : Sargis Khoobiar

It is certified that error appears in the above-identified patent and that said Letters Patent are hereby corrected as shown below:

Column 5, line 23 -- change "90'" to -- 90" --;

Column 6, line 41 -- insert "as" after the word "made".

Signed and Sealed this

Tenth Day of March 1981

[SEAL]

*Attest:*

RENE D. TEGTMEYER

*Attesting Officer*     *Acting Commissioner of Patents and Trademarks*